(12) United States Patent
Heike et al.

(10) Patent No.: US 6,698,296 B2
(45) Date of Patent: Mar. 2, 2004

(54) USE OF A CYLINDRICAL TEST BODY

(75) Inventors: Uwe Heike, Rellingen (DE); Ingo Weiss, Hamburg (DE); Klaus Bavendiek, Norderstedt (DE)

(73) Assignee: Yxlon International XRay GmbH, Hamburg (DE)

( * ) Notice: Subject to any disclaimer, the term of this patent is extended or adjusted under 35 U.S.C. 154(b) by 10 days.

(21) Appl. No.: 10/099,852

(22) Filed: Mar. 14, 2002

(65) Prior Publication Data

US 2002/0184748 A1 Dec. 12, 2002

(30) Foreign Application Priority Data

Mar. 16, 2001 (EP) .............................................. 01106636

(51) Int. Cl.$^7$ ................................................. G01N 3/02
(52) U.S. Cl. ....................................................... 73/856
(58) Field of Search .......................... 73/799, 760, 803, 73/804, 856, 857, 858, 859

(56) References Cited

U.S. PATENT DOCUMENTS

| | | | |
|---|---|---|---|
| 4,818,943 A | 4/1989 | Chandra | 324/318 |
| 5,165,050 A | 11/1992 | Goodenough et al. | 324/318 |
| 6,341,874 B1 * | 1/2002 | Rubin | 362/103 |
| 6,422,426 B1 * | 7/2002 | Robbins et al. | 222/158 |

OTHER PUBLICATIONS

J. Alison Noble, et al., "High Precision X–Ray Stereo for Automated 3–D CAD–Based Inspection", XP–000754935, IEEE Trans. on Robotics and Automation, vol. 14, No. 2, Apr. 1998, pp. 292–302.

Domingo Mery, et al., "Flaw Tracking in a Sequence of Digital X–Ray Images: a New Method of Automated Quality Control of Castings", XP–00966288, Manuskripteingang Jan. 18, 2000; zur Veröffentlichung angenommen: Feb. 2, 2000, pp. 160–165.

* cited by examiner

Primary Examiner—Max Noori
(74) Attorney, Agent, or Firm—Roberts & Roberts, LLP

(57) ABSTRACT

The invention relates to the use of a cylindrical test body with one or more spherical cavities for testing the function and defect recognition quality of systems for the automatic recognition of defects in castings and method for the manufacture thereof. All the prior art testing possibilities are not in accordance with practice and suffer from different advantages. The invention surprisingly obviates this problem by the use of a cylindrical test body with one or more spherical cavities for testing the function and defect recognition quality of systems for the automatic recognition of defects in castings and which is fixed on or in the casting to be tested. Thus, the invention has created test bodies or objects, which better approximate the shape of natural defects and which are simple and inexpensive to manufacture in reproducible manner. These test bodies contain one or more spherical cavities optionally having different sizes and positions.

18 Claims, 2 Drawing Sheets

T = THICKNESS OF THE TEST BODY

USE OF A CYLINDRICAL TEST BODY

BACKGROUND OF THE INVENTION

1. Field of the Invention

The invention relates to the use of a cylindrical test body with one or more spherical cavities for testing the function and defect recognition quality of systems for the visual or automatic recognition of defects in castings and a method for the manufacture thereof.

2. Description of the Related Art

Modern systems for the automatic recognition of defects in castings, so-called ADR systems (automatic defect recognition) must be able to reliably detect ever smaller defects. The smallest attenuations and interferences in the signal chain can lead to defects no longer being reliably detected. At the same time the presently used methods for enabling conclusions to be drawn concerning defects and defect sizes by means of 2D/3D filming, require an adaptation in accordance with practice, so that in the forefront of the interpretation of an ADR system a valid statement can be made concerning the possible recognition quality.

In conventionally used methods, the function of the system is tested with wire penetrameters, e.g. DIN 54109 or platinum double wire webs (standard EN 13068-3), or by means of inspection parts provided with clearly defined bores; or perforated plates applied to inspection parts, e.g. ASTM E-1025.

All these testing and inspection possibilities are not really in accordance with practice. The first unit only tests the resolution and cannot be used for detection purposes. The second unit is scarcely reproducible, because the drilling depths are individually set, the drilled hole is conical and as a result of the cylindrical shape of the hole or bore, the transmission direction has a considerable influence on recognition. The third possibility, using a penetrameter, suffers from the same problem that the detectable size of the objects is dependent to a significant extent on the transmission direction as a result of the cylindrical geometry. In addition, the sharp edges of the bores provide contrasts not in accordance with 3D defect practice. The first and third methods also suffer from the fact that the test bodies cannot be fixed to the part to be inspected in the installation and then allow an automatic installation calibration. Therefore the problem of the invention is to improve the testing and inspection possibilities for the operation and defect recognition quality of ADR systems, whilst providing an economic method for the manufacture of the test bodies used for this purpose.

Surprisingly this problem is solved by the use of a cylindrical test body with a spherical cavity for testing the function and defect recognition quality of systems for the automatic recognition of defects in castings and fixed on or in the casting to be tested.

The invention creates test objects or bodies, which better approximate the shape of natural defects and which can be manufactured easily and inexpensively in a reproducible manner. These test bodies contain one or more spherical cavities optionally of different sizes and positions. Thus, the invention makes it possible to obviate the use of wire penetrameters, defined conical bores and perforated plates.

The method of the invention for the manufacture of said cylindrical test body offers the three following alternatives:

1) a. Punching circular holes, whose diameter approximates in optimum manner the shape of a ball, in the center of a plurality of foil layers, which are made from the material of a casting to be tested. b. Superimposing the plurality of foil layers with the punched holes and adjacent to the foil layers with the smallest holes are superimposed foil layers without a hole. c. Pressing or bonding together the superimposed plurality of foil layers. or 2) a. Provision of two cylindrical test body pieces with the same diameter. b. Drilling a hemispherical recess in one end face of each cylindrical test body piece. c. Assembly by means of bonding of the test body pieces at the end faces thereof. or 3) a. provision of two cylindrical test body pieces with the same diameter. b. Provision of a circular recess in one test body piece and a corresponding circular insert in facing manner on the other test body piece and drilling a semicircular recess in facing sides of the test body piece or circular insert, and c. Pressing the circular insert into the circular recess.

SUMMARY OF THE INVENTION

The invention provides a cylindrical test body comprising one or more spherical cavities for testing the function and defect recognition quality of systems for the automatic recognition of defects in castings fixed on or in the casting to be tested.

The invention also provides a method for the manufacture of a cylindrical test body with one or more spherical cavities comprising I, II or III:

I. a) punching circular holes, whose diameter approximates in optimum manner the shape of a ball, in the center of a plurality of foil layers, which are made from the material of a casting to be tested, b) superimposing of the plurality of foil layers with the punched holes and adjacent to the foil layers with the smallest holes are superimposed foil layers without a hole, c) pressing or bonding together the superimposed plurality of foil layers;

II. a) provision of two cylindrical test body pieces with the same diameter, b) drilling a hemispherical recess in one end face of each cylindrical test body piece, c) assembly by means of bonding of the test body pieces at the end faces thereof;

III. a) provision of two cylindrical test body pieces with the same diameter. b) provision of a circular recess in one test body piece and a corresponding circular insert in facing manner on the other test body piece and drilling a semicircular recess in facing sides of the test body piece or circular insert, and c) pressing the circular insert into the circular recess.

The invention further provides cylindrical test body for testing the function and quality of a defect recognition system, which cylindrical test body is formed by the steps of I, II, or III:

I. a) providing a plurality of circular foil layers, which foil layers comprise a material of a casting to be tested; b) forming a circular hole in some of the foil layers, whereby the circular holes are sufficiently sized and aligned such that, upon superimposing the plurality of foil layers, the circular holes are capable of defining a central spherical cavity within the superimposed plurality of foil layers; c) superimposing the plurality of foil layers such that the circular holes define a central spherical cavity within the superimposed plurality of foil layers, and such that those foil layers with the smallest holes are superimposed against foil layers without holes, and d) attaching the superimposed plurality of foil layers to form a cylindrical test body having a central spherical cavity;

II. a) providing first and second cylindrical test body pieces of substantially the same diameter, wherein each test body piece has an end face which faces the other test body piece; b) forming a hemispherical recess within in one end face of each cylindrical test body piece, and c) attaching the end face of the first test body piece to the end face of the second test body piece to thereby form a cylindrical test body, and wherein the hemispherical recesses are sufficiently aligned to thereby define a central spherical cavity within the cylindrical test body;

III. a) providing first and second test body pieces having a height H, thickness T, and diameter Dm, and each test body piece further comprising a hemispherical recess having a diameter Dz; b) providing a spherical insert having substantially the same diameter as the hemispherical recesses; c) placing the spherical insert within the hemispherical recess of the first test body piece such that a first half of the spherical insert is within the hemispherical recess and a second half of the spherical insert faces the second test body piece; and d) placing the second test body piece onto the second half of the spherical insert to thereby attach the first and second test body pieces, thus forming a cylindrical test body with a central spherical insert.

The invention still further provides a process for testing the function and quality of a defect recognition system, which process comprises the steps of: i) providing a cylindrical test body for testing the function and quality of a defect recognition system, which cylindrical test body is formed by the steps of I, II, or III:

I. a) providing a plurality of circular foil layers, which foil layers comprise a material of a casting to be tested; b) forming a circular hole in some of the foil layers, whereby the circular holes are sufficiently sized and aligned such that, upon superimposing the plurality of foil layers, the circular holes are capable of defining a central spherical cavity within the superimposed plurality of foil layers; c) superimposing the plurality of foil layers such that the circular holes define a central spherical cavity within the superimposed plurality of foil layers, and such that those foil layers with the smallest holes are superimposed against foil layers without holes, and d) attaching the superimposed plurality of foil layers to form a cylindrical test body having a central spherical cavity;

II. a) providing first and second cylindrical test body pieces of substantially the same diameter, wherein each test body piece has an end face which faces the other test body piece; b) forming a hemispherical recess within in one end face of each cylindrical test body piece, and c) attaching the end face of the first test body piece to the end face of the second test body piece to thereby form a cylindrical test body, and wherein the hemispherical recesses are sufficiently aligned to thereby define a central spherical cavity within the cylindrical test body;

III. a) providing first and second test body pieces, each having a height H, thickness T, and diameter Dm, and each test body piece further comprising a hemispherical recess having a diameter Dz, such that the first and second test body pieces are capable of forming a central spherical cavity upon attaching the test body pieces together; b) providing a spherical insert having substantially the same diameter as the hemispherical recesses; c) placing the spherical insert within the hemispherical recess of the first test body piece such that a first half of the spherical insert is within the hemispherical recess and a second half of the spherical insert faces the second test body piece; and d) placing the second test body piece onto the second half of the spherical insert to thereby attach the first and second test body pieces, thus forming a cylindrical test body having a central spherical cavity which contains the spherical insert; ii) providing an automatic defect recognition system comprising a defect detector; iii) measuring the spherical cavity of the cylindrical test body in three dimensions with the defect detector, to test the image quality of the defect detector and to calibrate the defect detector.

BRIEF DESCRIPTION OF THE DRAWINGS

FIG. 1a shows a perspective view of a test body used according to the invention in the structure based on the foil principle.

FIG. 1b shows a cross-sectional view of the test body of FIG. 1a.

FIG. 2a shows a diagrammatic perspective view of a further, not yet assembled test body based on the half-body principle.

FIG. 2b shows a diagrammatic cross-sectional view through the test body of FIG. 2a.

FIG. 4a shows a perspective view of another embodiment of a test body according to the invention with several spherical cavities prior to assembly.

FIG. 4b shows a horizontal section through the test body of FIG. 4a.

DETAILED DESCRIPTION OF THE PREFERRED EMBODIMENT

Figures 1A, 1B:
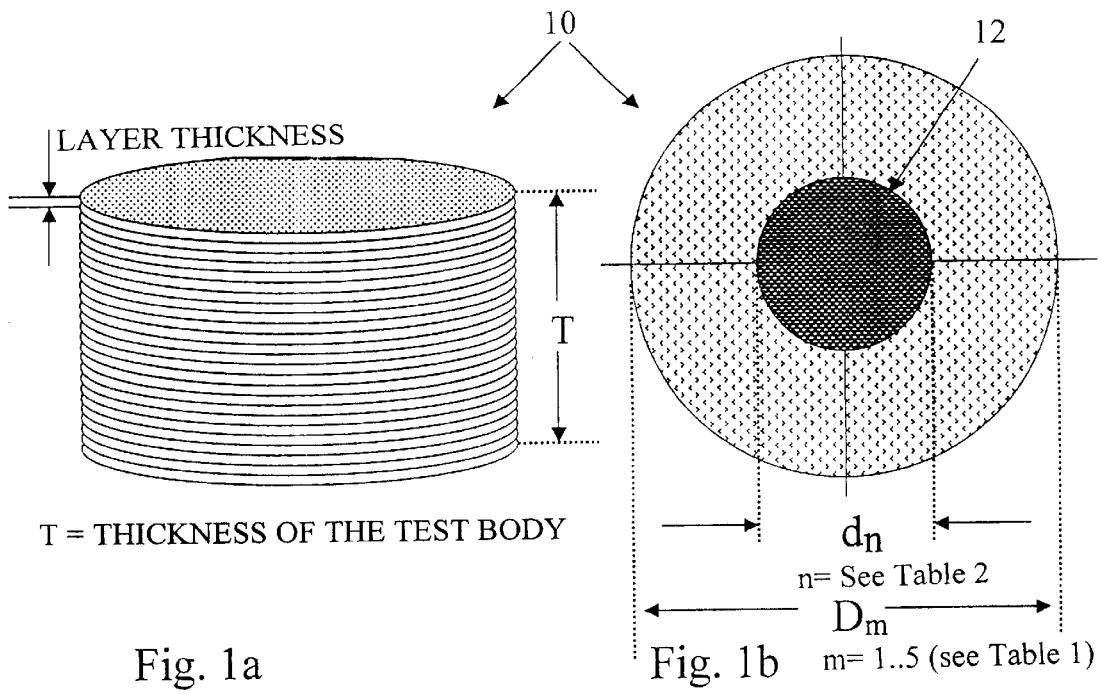

In FIG. 1a the cylindrical test body produced according to the first manufacturing variant carries the reference numeral 10. It has 20 foil layers, which are congruently superimposed and in all give a thickness=T of the test body 10, the layer thickness of the individual foils being e.g. 20 or 50 $\mu$m. It is clear that other values are readily conceivable.

In FIG. 1b the hole punched centrally in each coil carries the reference numeral 12. The diameter for the foil or hole (Dm, dn) is given in Table 1 or 2.

It is possible to build up from a set of 100 foils having in each case a thickness of e.g. 20 $\mu$m and punched out holes with diameters, as shown in Table 2, from 0.2 mm to the maximum diameter, all desired cavity sizes for a test body with a thickness of 2 mm. The superimposed foil layers can be pressed together at each corner by two plastic or aluminum plates using in each case one screw or are bonded with an adhesive, which is scarcely X-ray absorbing. The foil layer material corresponds to that to be tested, e.g. aluminum. It is clear that the test bodies are fixed on or in the casting to be tested at an appropriate point.

Figures 2A, 2B:
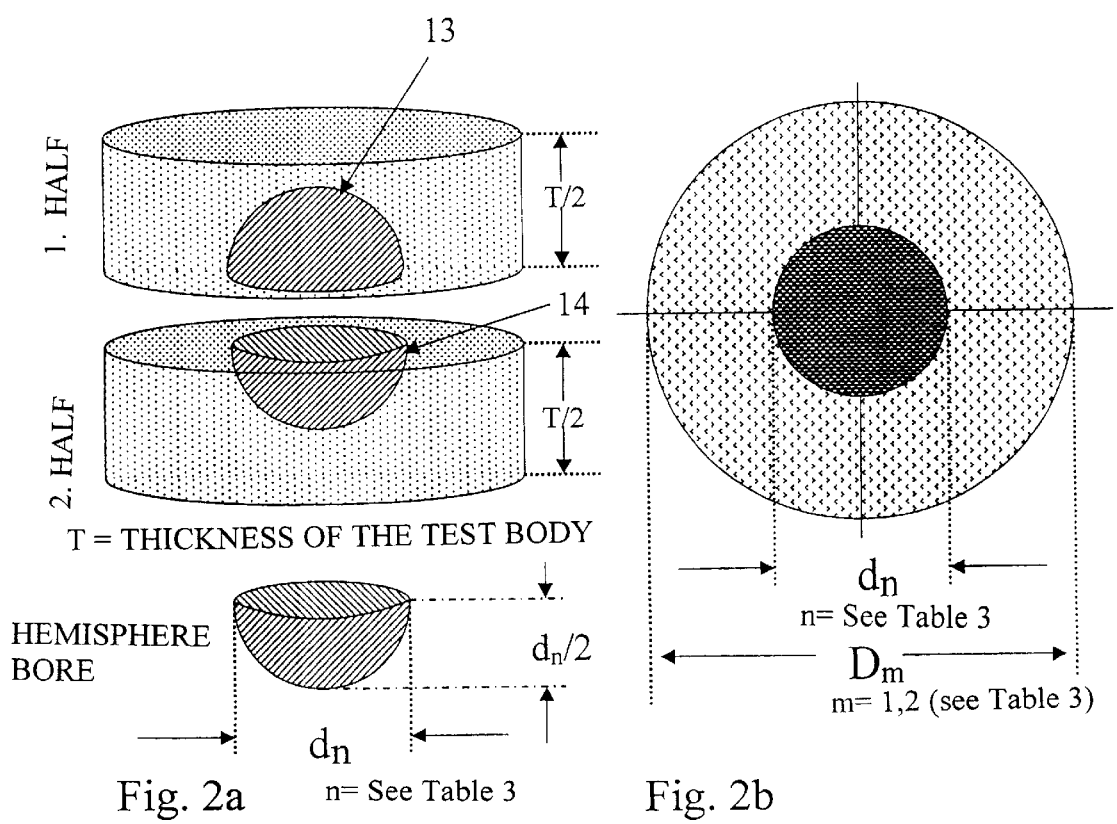

In the second method variant, in two cylindrical test body pieces are made in each case two hemispherical holes or recesses 13, 14, so that a spherical cavity is obtained on assembly, as shown in FIG. 2a. The body pieces are then bonded together.

Figure 3:
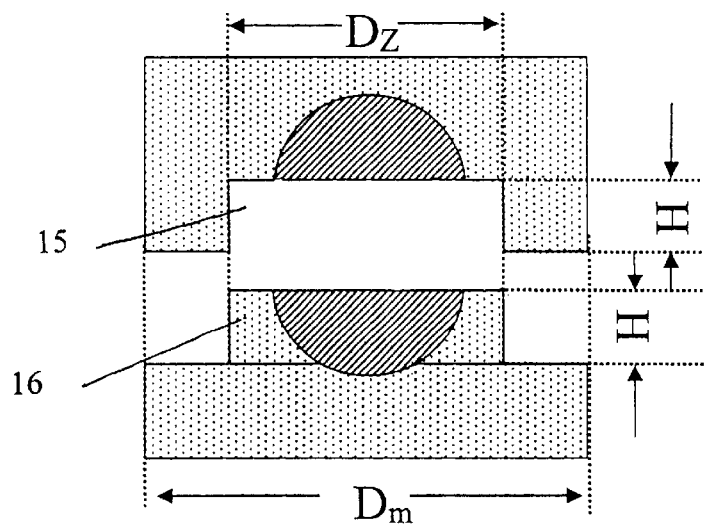
FIG. 3 shows a diagrammatic cross-sectional view through another embodiment of a test body according to the invention prior to its assembly.

According to another embodiment, for adhesive-free assembly, a somewhat larger circular insert 16 can be inserted in the test body piece and is then pressed together with the other test body piece having a circular recess 15. The basic structure is shown in FIG. 3.

Figures 4A, 4B:
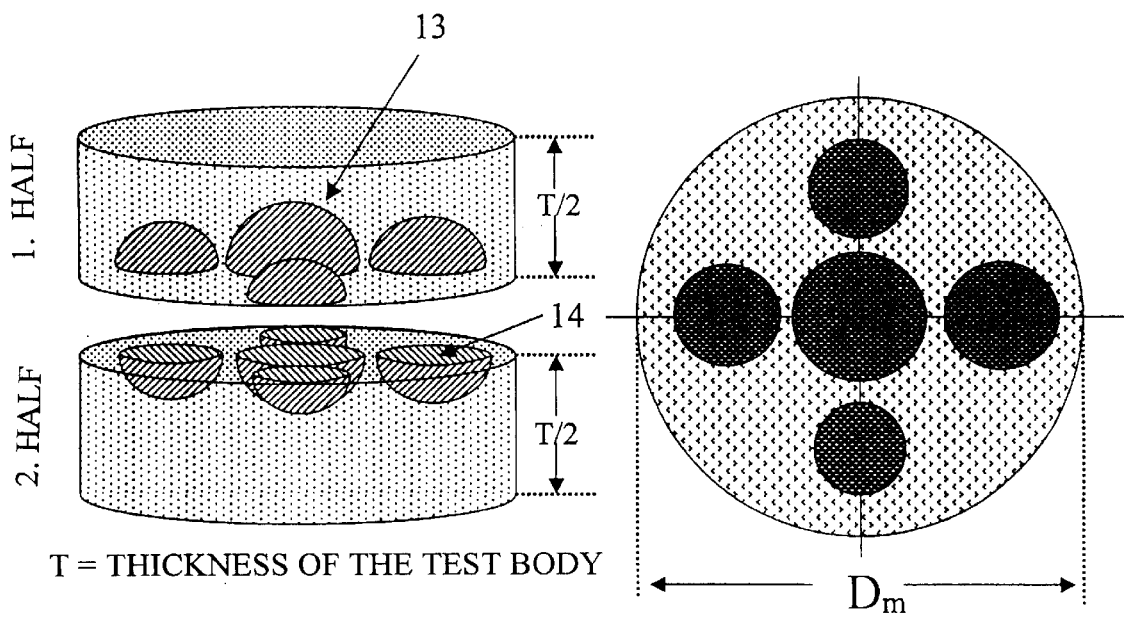

In order to be able to simulate defect groups, it is also possible to make several holes with the same or different diameters (cf. FIG. 4a+b). When using different diameters it is possible to determine with a single test body the defect recognizability limit quantity.

Fundamentally the test body according to the invention is cylindrical or rod-shaped, so that by means of a bore identical to the external diameter the test body can be introduced positively into a casting to be tested. The thus prepared casting to be tested can be used as a measurement part for an X-ray system. On passing through the system information is provided as to whether defects of this size can be reliably detected by the system.

The use of a test body according to the invention offers the following advantages:

The detectable defect size is independent of the transmission direction (because there are spherical 3D cavities). There is a defect approximation in 3D instead of 2D—test bodies for 3D calibration with potential for 3D defect depth measurement of defects. The test body tests both the image quality of the detector and the detection by the software. Optionally groups of identical cavities can be made in order to e.g. simulate shrink holes and only in this way can group defect recognition be measured. It is also possible to make groups of different cavities in order in this way to determine the recognizability limit with a single test object (similar to line pattern with 2D). With considerable variations, test bodies are easy, inexpensive and reproducible to manufacture.

TABLE 1

Example for Test Body Diameter ($D_m$) for Various Thicknesses T by the Foil Method

| Diameter of the Test Body in µm | | Thickness T in mm | | | |
|---|---|---|---|---|---|
| | | 1 | 2 | 5 | 10 |
| Diameter (D1) | 5 | X | X | | |
| Diameter (D2) | 10 | X | X | X | |
| Diameter (D3) | 20 | X | X | X | |
| Diameter (D5) | 40 | | | X | X |
| Diameter (D5) | 60 | | | | X |

Construction of the Test Body from Layers with thickness of 20 to 50 mm (See Table 2)
Remarks:
The Tables only show the first halves of the layers since the construction is symmetrical around the middle plates.

TABLE 2

Hole Diameter $d_n$ of the individual Films With T = 2 mm Thickness of the test Body

| | 2 mm Thickness 0.2 Hole diameter $d_n$ | | Units in µm, if not otherwise described | | | | | | | |
|---|---|---|---|---|---|---|---|---|---|---|
| Layer/µm | 0.2 | 0.4 | 0.6 | 0.8 | 1 | 1.2 | 1.4 | 1.6 | 1.8 | 2 |
| 20 | | | | | | | | | | |
| 0 | 0 | 0 | 0 | 0 | 0 | 0 | 0 | 0 | 0 | 0 |
| 20 | 0 | 0 | 0 | 0 | 0 | 0 | 0 | 0 | 0 | 282 |
| 40 | 0 | 0 | 0 | 0 | 0 | 0 | 0 | 0 | 0 | 486 |
| 60 | 0 | 0 | 0 | 0 | 0 | 0 | 0 | 0 | 0 | 624 |
| 80 | 0 | 0 | 0 | 0 | 0 | 0 | 0 | 0 | 0 | 735 |
| 100 | 0 | 0 | 0 | 0 | 0 | 0 | 0 | 0 | 0 | 829 |
| 120 | 0 | 0 | 0 | 0 | 0 | 0 | 0 | 0 | 268 | 912 |
| 140 | 0 | 0 | 0 | 0 | 0 | 0 | 0 | 0 | 461 | 986 |
| 160 | 0 | 0 | 0 | 0 | 0 | 0 | 0 | 0 | 592 | 1054 |
| 180 | 0 | 0 | 0 | 0 | 0 | 0 | 0 | 0 | 696 | 1116 |
| 200 | 0 | 0 | 0 | 0 | 0 | 0 | 0 | 0 | 785 | 1173 |
| 220 | 0 | 0 | 0 | 0 | 0 | 0 | 0 | 252 | 862 | 1226 |
| 240 | 0 | 0 | 0 | 0 | 0 | 0 | 0 | 434 | 932 | 1276 |
| 260 | 0 | 0 | 0 | 0 | 0 | 0 | 0 | 557 | 995 | 1323 |
| 280 | 0 | 0 | 0 | 0 | 0 | 0 | 0 | 655 | 1053 | 1367 |
| 300 | 0 | 0 | 0 | 0 | 0 | 0 | 0 | 737 | 1106 | 1408 |
| 320 | 0 | 0 | 0 | 0 | 0 | 0 | 236 | 810 | 1156 | 1448 |
| 340 | 0 | 0 | 0 | 0 | 0 | 0 | 405 | 874 | 1202 | 1485 |
| 360 | 0 | 0 | 0 | 0 | 0 | 0 | 520 | 933 | 1245 | 1520 |
| 380 | 0 | 0 | 0 | 0 | 0 | 0 | 610 | 986 | 1285 | 1553 |
| 400 | 0 | 0 | 0 | 0 | 0 | 0 | 687 | 1035 | 1323 | 1585 |
| 420 | 0 | 0 | 0 | 0 | 0 | 218 | 753 | 1081 | 1359 | 1615 |
| 440 | 0 | 0 | 0 | 0 | 0 | 375 | 813 | 1123 | 1393 | 1643 |
| 460 | 0 | 0 | 0 | 0 | 0 | 480 | 866 | 1162 | 1425 | 1670 |
| 480 | 0 | 0 | 0 | 0 | 0 | 562 | 915 | 1198 | 1455 | 1696 |
| 500 | 0 | 0 | 0 | 0 | 0 | 632 | 959 | 1233 | 1483 | 1720 |
| 520 | 0 | 0 | 0 | 0 | 199 | 693 | 1000 | 1265 | 1510 | 1743 |
| 540 | 0 | 0 | 0 | 0 | 341 | 746 | 1037 | 1295 | 1535 | 1765 |
| 560 | 0 | 0 | 0 | 0 | 436 | 794 | 1072 | 1323 | 1559 | 1786 |
| 580 | 0 | 0 | 0 | 0 | 510 | 837 | 1105 | 1349 | 1581 | 1806 |
| 600 | 0 | 0 | 0 | 0 | 572 | 876 | 1135 | 1374 | 1602 | 1824 |
| 620 | 0 | 0 | 0 | 178 | 626 | 912 | 1163 | 1397 | 1622 | 1842 |
| 640 | 0 | 0 | 0 | 304 | 673 | 945 | 1188 | 1419 | 1641 | 1858 |
| 660 | 0 | 0 | 0 | 387 | 714 | 975 | 1212 | 1439 | 1658 | 1873 |
| 680 | 0 | 0 | 0 | 452 | 751 | 1002 | 1235 | 1458 | 1675 | 1888 |
| 700 | 0 | 0 | 0 | 506 | 785 | 1027 | 1255 | 1475 | 1690 | 1901 |

TABLE 2-continued

Hole Diameter $d_n$ of the individual Films With T = 2 mm Thickness of the test Body

| Layer/µm | 2 mm Thickness Hole diameter $d_n$ 0.2 | 0.4 | Units in µm, if not otherwise described 0.6 | 0.8 | 1 | 1.2 | 1.4 | 1.6 | 1.8 | 2 |
|---|---|---|---|---|---|---|---|---|---|---|
| 720 | 0 | 0 | 154 | 551 | 815 | 1051 | 1274 | 1491 | 1704 | 1914 |
| 740 | 0 | 0 | 262 | 590 | 842 | 1072 | 1292 | 1506 | 1717 | 1926 |
| 760 | 0 | 0 | 332 | 624 | 866 | 1091 | 1308 | 1520 | 1729 | 1936 |
| 780 | 0 | 0 | 385 | 655 | 888 | 1108 | 1322 | 1532 | 1740 | 1946 |
| 800 | 0 | 0 | 428 | 681 | 908 | 1124 | 1336 | 1544 | 1750 | 1955 |
| 820 | 0 | 125 | 464 | 704 | 925 | 1138 | 1347 | 1554 | 1759 | 1964 |
| 840 | 0 | 211 | 494 | 724 | 940 | 1151 | 1358 | 1563 | 1768 | 1971 |
| 860 | 0 | 265 | 520 | 742 | 954 | 1162 | 1367 | 1572 | 1775 | 1977 |
| 880 | 0 | 304 | 541 | 757 | 966 | 1171 | 1376 | 1579 | 1781 | 1983 |
| 900 | 0 | 334 | 558 | 769 | 975 | 1180 | 1383 | 1585 | 1787 | 1988 |
| 920 | 87 | 357 | 572 | 779 | 984 | 1186 | 1388 | 1590 | 1791 | 1992 |
| 940 | 143 | 375 | 583 | 788 | 990 | 1192 | 1393 | 1594 | 1795 | 1995 |
| 960 | 173 | 387 | 592 | 794 | 995 | 1196 | 1396 | 1597 | 1797 | 1997 |
| 980 | 191 | 395 | 597 | 798 | 998 | 1198 | 1399 | 1599 | 1799 | 1999 |
| 1000 | 199 | 399 | 600 | 800 | 1000 | 1200 | 1400 | 1600 | 1800 | 2000 |

| | | Thickness T in mm | | | |
|---|---|---|---|---|---|
| Diameter $D_m$ of the Test body in mm | | 1 | 2 | 5 | 10 |
| Diameter (D1) | 15 | X | X | X | |
| Diameter (D-5) | 12 | | X | X | X |

Construction of the Test Body of 2 identical halves.
Remarks:
1.: The Penetrameter was adhered together from 2 identical parts; The adhesive may not contain metals (FIG. 2).
2.: By the construction according to FIG. 3, the two halves were pressed together. The diameter $D_z$ amounts to ⅝ of $d_m$ the height H corresponds to ⅔ of thickness T.

TABLE 3

Hole Diameter $d_n$ for the various Embodiment of the Test Body

| | Thickness of the Test Body | Bored Hemispherical measure $d_n$ in mm; 0.2 | 0.3 | 0.4 | 0.5 | 0.6 | 0.7 | 0.8 | 0.9 | 1 | 1.1 | 1.2 | 1.3 | 1.4 | 1.5 | 1.6 | 1.8 | 2 |
|---|---|---|---|---|---|---|---|---|---|---|---|---|---|---|---|---|---|---|
| Diameter D1 | 5 | 1 | # | # | # | # | # | # | # | | | | | | | | | | |
| Diameter D1 | 5 | 2 | # | # | # | # | # | # | # | # | # | # | # | # | # | # | # | | |
| Diameter D1 | 5 | 5 | # | # | # | # | # | # | # | # | # | # | # | # | # | # | # | # | |
| Diameter D2 | 12 | 2 | | | # | # | # | # | # | # | # | # | # | # | # | # | # | | |
| Diameter D2 | 12 | 5 | | | | | | | | # | # | # | # | # | # | # | # | # | # |
| Diameter D2 | 12 | 10 | | | | | | | | | | | | | | | | | # |
| Diameter D1 | 5 | 1 | | | | | | | | | | | | | | | | | |
| Diameter D1 | 5 | 2 | | | | | | | | | | | | | | | | | |
| Diameter D1 | 5 | 5 | # | # | # | # | # | # | # | # | | | | | | | | | |
| Diameter D2 | 12 | 2 | | | | | | | | | | | | | | | | | |
| Diameter D2 | 12 | 5 | # | # | # | # | # | # | # | # | | | | | | | | | |
| Diameter D2 | 12 | 10 | # | # | # | # | # | # | # | # | # | # | # | # | # | # | # | # | |

Only the values marked # were produced

While the present invention has been particularly shown and described with reference to preferred embodiments, it will be readily appreciated by those of ordinary skill in the art that various changes and modifications may be made without departing from the spirit and scope of the invention. It is intended that the claims be interpreted to cover the disclosed embodiment, those alternatives which have been discussed above and all equivalents thereto.

What is claimed is:

1. A cylindrical test body for testing the function and quality of a defect recognition system, comprising a plurality of circular foil layers, which foil layers comprise a material of a casting to be tested; whereby a circular hole in some of the foil layers is formed, whereby the circular holes are sufficiently sized and aligned such that, upon superimposing the plurality of foil layers, the circular holes define a central spherical cavity within the superimposed plurality of foil layers; and those foil layers with the smallest holes are superimposed against foil layers without holes.

2. The cylindrical test body of claim 1 wherein the foil layers or the test body pieces comprise aluminum.

3. The cylindrical test body of claim 1, wherein the foil layers or the test body pieces are attached via a metal-free adhesive.

4. The cylindrical test body of claim 1, wherein the diameter (Dz) of the recess is about ⅝ of the diameter (Din) of the test body pieces, and wherein the height (H) is about ⅔ of the thickness (T).

5. A process for testing the function and quality of a defect recognition system, which process comprises the steps of:

i) providing a cylindrical test body for testing the function and quality of a defect recognition system, which cylindrical test body is formed by the steps of I, II, or III:

I.
  a) providing a plurality of circular foil layers, which foil layers comprise a material of a casting to be tested;
  b) forming a circular hole in some of the foil layers, whereby the circular holes are sufficiently sized and aligned such that, upon superimposing the plurality of foil layers, the circular holes are capable of defining a central spherical cavity within the superimposed plurality of foil layers;
  c) superimposing the plurality of foil layers such that the circular holes define a central spherical cavity within the superimposed plurality of foil layers, and such that those foil layers with the smallest holes are superimposed against foil layers without holes, and
  d) attaching the superimposed plurality of foil layers to form a cylindrical test body having a central spherical cavity;

II.
  a) providing first and second cylindrical test body pieces of substantially the same diameter, wherein each test body piece has an end face which faces the other test body piece;
  b) forming a hemispherical recess within in one end face of each cylindrical test body piece, and
  c) attaching the end face of the first test body piece to the end face of the second test body piece to thereby form a cylindrical test body, and wherein the hemispherical recesses are sufficiently aligned to thereby define a central spherical cavity within the cylindrical test body;

III.
  a) providing first and second test body pieces, each having a height H, thickness T, and diameter Dm, and each test body piece further comprising a hemispherical recess having a diameter Dz, such that the first and second test body pieces are capable of forming a central spherical cavity upon attaching the test body pieces together;
  b) providing a spherical insert having substantially the same diameter as the hemispherical recesses;
  c) placing the spherical insert within the hemispherical recess of the first test body piece such that a first half of the spherical insert is within the hemispherical recess and a second half of the spherical insert faces the second test body piece; and
  d) placing the second test body piece onto the second half of the spherical insert to thereby attach the first and second test body pieces, thus forming a cylindrical test body having a central spherical cavity which contains the spherical insert;

ii) providing an automatic defect recognition system comprising a defect detector;

iii) measuring the spherical cavity of the cylindrical test body in three dimensions with the defect detector, to test the image quality of the defect detector and to calibrate the defect detector.

6. The process of claim 5 wherein groups of identical cavities are formed within the cylindrical test body to thereby measure group defect recognition of the defect detector.

7. The process of claim 5 wherein a plurality of cavities are formed within the cylindrical test body to thereby determine the recognizability limit of the defect detector using a single cylindrical test body.

8. The process of claim 5 wherein the foil layers or the test body pieces comprise aluminum.

9. The process of claim 5 wherein the foil layers or the test body pieces are attached via a metal-free adhesive.

10. The process of claim 9 wherein the diameter (Dz) of the recess is about 5/8 of the diameter (Din) of the test body pieces, and wherein the height (H) is about 2/8 of the thickness (T).

11. A cylindrical test body for testing the function and quality of a defect recognition system, comprising first and second cylindrical test body pieces of substantially the same diameter, wherein each test body piece has an end face which faces the other test body piece; having a hemispherical recess within each end face of each cylindrical test body piece, and the end face of the first test body piece is attached to the end face of the second test body piece to thereby form a cylindrical test body, and wherein the hemispherical recesses are sufficiently aligned to thereby define a central spherical cavity within the cylindrical test body.

12. The cylindrical test body of claim 11 wherein the foil layers or the test body pieces comprise aluminum.

13. The cylindrical test body of claim 11, wherein the foil layers or the test body pieces are attached via a metal-free adhesive.

14. The cylindrical test body of claim 11, wherein the diameter (Dz) of the recess is about 5/8 of the diameter (Dm) of the test body pieces, and wherein the height (H) is about 2/8 of the thickness (T).

15. A cylindrical test body for testing the function and quality of a defect recognition system, comprising first and second test body pieces having a height H, thickness T, and diameter Dm, and each test body piece further comprising a hemispherical recess having a diameter Dz smaller than the diameter Dm; a spherical insert having substantially the same diameter as the hemispherical recesses; whereby the spherical insert is located within the hemispherical recess of the first test body piece such that a first half on the spherical insert is within the hemispherical recess and a second half of the spherical insert is within the hemispherical recess of the second test body piece; and the first test body piece is attached to the second test body piece, thus forming a cylindrical test body with a central spherical insert.

16. The cylindrical test body of claim 15 wherein the foil layers or the test body pieces comprise aluminum.

17. The cylindrical test body of claim 15, wherein the foil layers or the test body pieces are attached via a metal-free adhesive.

18. The cylindrical test body of claim 15, wherein the diameter (Dz) of the recess is about 5/8 of the diameter (Dm) of the test body pieces, and wherein the height (H) is about 2/8 of the thickness (T).

* * * * *